(12) United States Patent
Andersen et al.

(10) Patent No.: US 8,506,535 B2
(45) Date of Patent: Aug. 13, 2013

(54) GAS VENT VALVE ASSEMBLY

(75) Inventors: Eric Andersen, Braintree, MA (US);
Rene Robert, West Warwick, RI (US);
Gary Searle, Norfolk, MA (US);
Vincent Waldron, Cohasset, MA (US)

(73) Assignee: Smith Medical ASD, Inc., Rockland, MA (US)

(*) Notice: Subject to any disclaimer, the term of this patent is extended or adjusted under 35 U.S.C. 154(b) by 624 days.

(21) Appl. No.: 12/320,348

(22) Filed: Jan. 23, 2009
(Under 37 CFR 1.47)

(65) Prior Publication Data
US 2009/0192447 A1    Jul. 30, 2009

Related U.S. Application Data

(60) Provisional application No. 61/006,668, filed on Jan. 25, 2008.

(51) Int. Cl.
*A61M 5/14*    (2006.01)

(52) U.S. Cl.
USPC .............. 604/254; 604/113; 604/127

(58) Field of Classification Search
USPC ............ 604/6.13, 27, 30, 45, 80, 113, 114, 604/122, 127, 247, 251–255; 607/104, 105, 607/106; 96/158, 168; 137/393, 399, 409, 137/429, 430, 433; 222/66, 67, 181.1, 444, 222/453, 456, 571
See application file for complete search history.

(56) References Cited

U.S. PATENT DOCUMENTS

| | | |
|---|---|---|
| 3,543,752 A | 12/1970 | Hesse et al. |
| 4,320,001 A | 3/1982 | Le Boeuf |

(Continued)

FOREIGN PATENT DOCUMENTS

CN    1439434    9/2003

*Primary Examiner* — Kami A Bosworth
(74) *Attorney, Agent, or Firm* — Louis Woo

(57) ABSTRACT

A gas vent valve assembly may be attached or incorporated to a disposable fluid transfer set used with a fluid warmer to administer an infusate to a patient. The gas vent valve assembly has a housing having a fluid inlet, a gas outlet and a fluid outlet. The gas outlet is located at the top of the housing while the fluid outlet is located at the bottom of the housing. The fluid inlet is located at a side lower portion of the housing. Inside the housing is an actuator float that has an upper seal and a lower seal. The dimension of the float relative to the chamber of the housing is such that the float is freely movable within the housing to an upper position whereby its upper seal closes the gas outlet while the fluid outlet is opened, and to a lower position whereby its lower seal closes the fluid outlet and the gas outlet is opened. The movement of the float is dependent on the respective amounts of air and fluid in the housing, and the buoyancy of the float relative to the fluid in the housing. When a predetermined volume of air gets inside the housing, the float sinks to its lower position to close the fluid outlet and open the gas outlet, so that the air inside the housing is vented to atmosphere while fluid is prevented from being output to the patient. When the amount of gas in the chamber has been reduced to a given volume, with a corresponding increase in the amount of fluid in the housing, the float is raised to open the fluid outlet, thereby enabling the fluid inside the housing to be output to the patient. At that time, the gas outlet is shut to prevent any reverse inflow of air into the housing.

15 Claims, 5 Drawing Sheets

(56) References Cited

U.S. PATENT DOCUMENTS

| | | |
|---|---|---|
| 4,678,460 A | 7/1987 | Rosner |
| 5,460,603 A | 10/1995 | DeSantis |
| 6,213,986 B1 | 4/2001 | Darling, Jr. |
| 6,229,957 B1 * | 5/2001 | Baker .......................... 392/470 |
| 6,595,957 B1 | 7/2003 | Griffiths et al. |
| 2005/0171491 A1 | 8/2005 | Minh Miner et al. |
| 2007/0173759 A1 | 7/2007 | Augustine et al. |

* cited by examiner

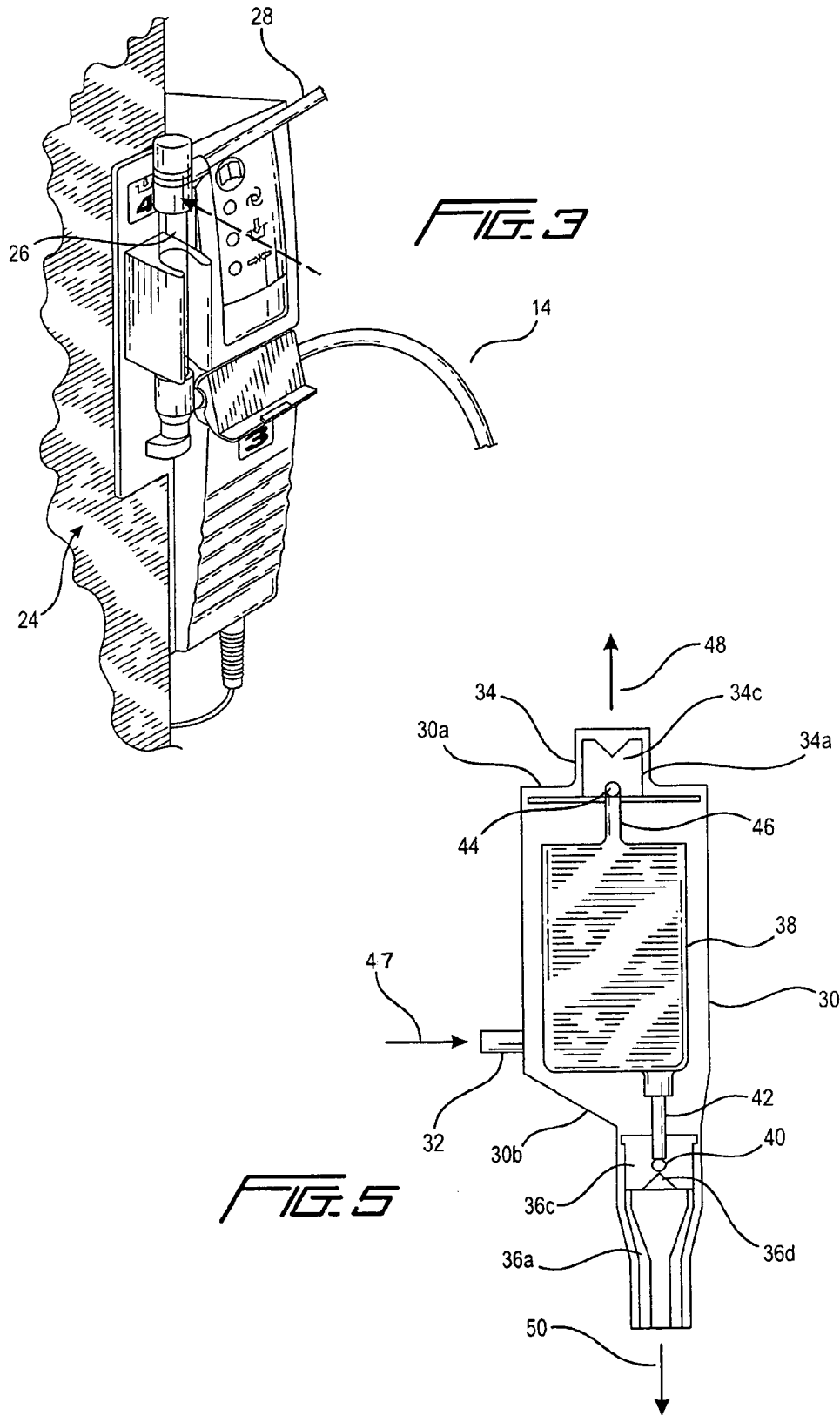

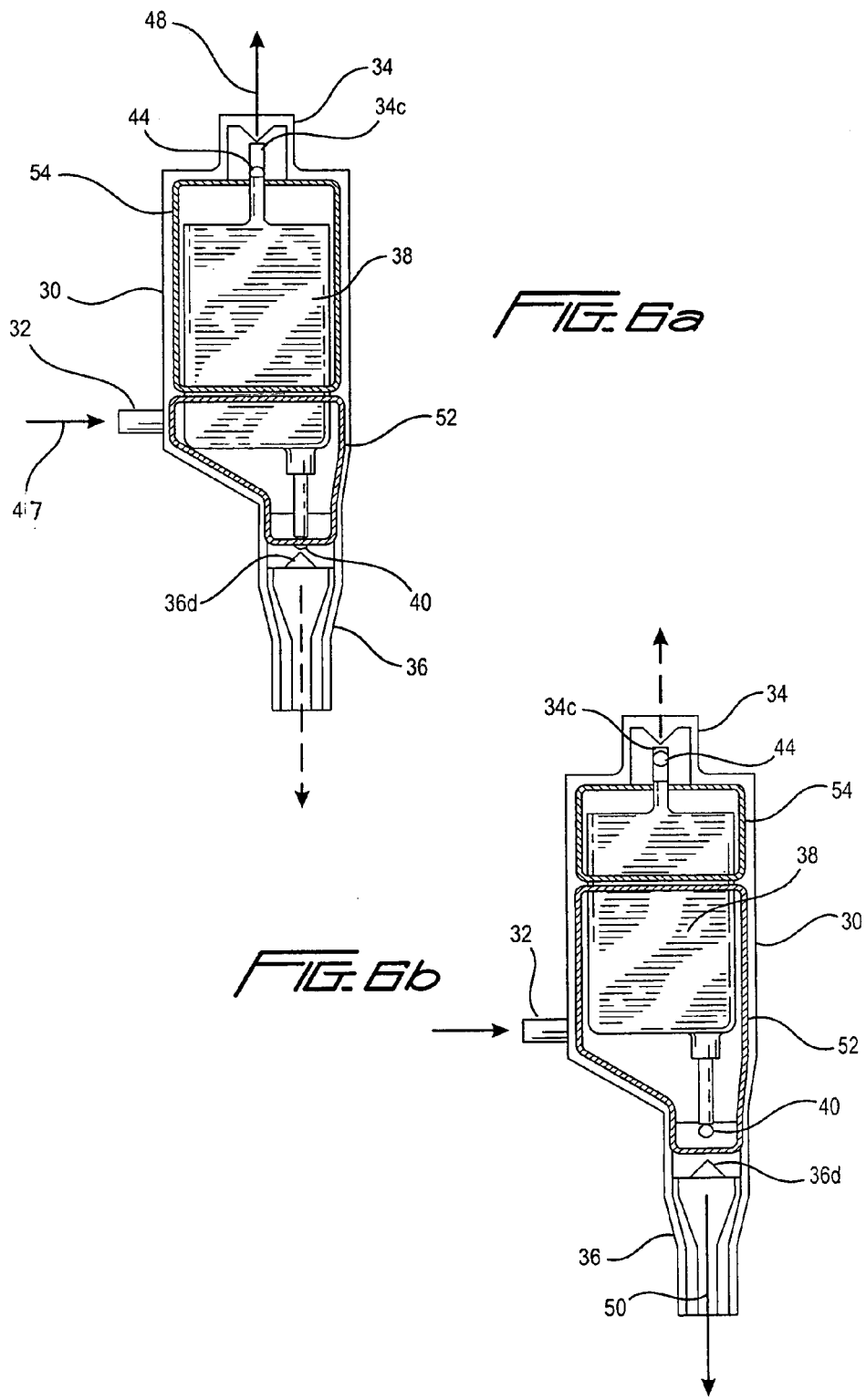

GAS VENT VALVE ASSEMBLY

FIELD OF THE INVENTION

The present invention relates to a device for eliminating gases or air that may be trapped within an intravenous (IV) tube set used to provide physiological or cellular fluids to a patient.

BACKGROUND OF THE INVENTION

When physiological or cellular fluids are administered to a patient, it is imperative that foreign particles and gas bubbles or air emboli that may be trapped in the fluids be removed. In the prior art, these fluids are passed through a filter before being administered to the patient.

One prior art filter is disclosed in U.S. Pat. No. 4,662,906. This filter includes a structure that first separates the gas from the fluid by introducing a vortex flow into the fluid. The gas bubbles that are separated from the fluid are moved into a chamber that is formed in part by a hydrophobic membrane, so that the gas exits to the atmosphere through the membrane. The fluid is then passed through a defoaming sponge, treated with an anti-foaming agent, so that any remaining gas is separated from the fluid. After exit from the sponge material into cylindrical element located within a storage reservoir, the remaining gas rises to the chamber and passes through the hydrophobic membrane to the atmosphere.

Anther prior art filter, assigned to the assignee of the instant application, is disclosed in U.S. Pat. No. 4,900,308. There, the filter has a plenum sufficiently large so that the downward velocity of fluid is less than the upward velocity of gas bubbles that form in the fluid. A hydrophobic membrane covers the top of the plenum, so that, as the gas rises to the top of the plenum it is separated from the fluid and exits to the atmosphere through the hydrophobic membrane. This device relies on the phenomenon that the downward flow velocity for a fluid is less than the rate at which a bubble of gas to be removed will rise through the fluid. There is therefore no control with respect to the venting of the gas to atmosphere or the administration of the fluid to the patient. The disclosure of the '308 application is incorporated by reference herein.

Another gas elimination device, also assigned to the assignee of the instant application, is disclosed in U.S. Pat. No. 5,707,431. In the '431 gas elimination device, a cylindrical chamber is divided radially into two parts by a cylindrical filter centrally located within the chamber. A fluid inlet is located such that the input fluid is directed tangentially to the outer part of the chamber to create a vortex flow, which is stopped by passage of the fluid through the filter. The vortex motion causes the gas contained in the fluid to be separated from the fluid and rises to the top of the outer portion of the chamber. The top of the chamber is covered by a hydrophobic membrane, which allows the gas to exit the chamber to the atmosphere. A shut-off valve in the form of a float has a bottom end that engages the fluid output when there is adequate fluid present in the device. The '431 device therefore requires that a filter be used to divide radially into two parts a cylindrical chamber so that the gas in the fluid is removable therefrom. The disclosure of the '421 patent is incorporated by reference herein.

SUMMARY OF THE PRESENT INVENTION

The gas vent valve assembly of the present invention is designed and adapted for use in an intravenous tube (IV) set that is disposable after use. The IV set, which is connected to a physiological fluid heater, such as for example any one of the systems H-1025, H-1200 and H-1000 High Flow Blood and Fluid Level 1 warmers sold by the assignee of the instant invention. The gas vent valve assembly is added to a conventional disposable unit so that an extra level of protection is provided to the patient by preventing gas and air emboli that may be in the infusate from being administered into the patient.

The gas vent valve assembly has a valve body housing that has a fluid inlet at a side thereof, a gas outlet at its top and a fluid outlet at its bottom. An actuator that may be a float dimensioned to be freely movable within the valve housing is positioned within the chamber of the housing. The float may be sealed, if it is hollow, to increase the buoyancy. Alternatively, the float may be made from a solid material, for example plastic, that has the required buoyancy. In any event, the float has a lower surface where there is an extension or a shaft. At the end of the shaft is a seal mechanism that may be in the form of a ball or sphere or some other configuration that allows it to engage in a seal tight manner to a seat provided at the fluid outlet of the valve housing. At the top surface of the float there is an extension or upper shaft. At the top of the upper shaft there is a seal mechanism that may also be in the form of a ball or a sphere or some other shape that allows it to sealingly engage with an upper seat at the gas outlet at the top of the valve housing. The upper seal may not be needed if a hydrophobic membrane is placed over the gas outlet. However, when an upper seal is used in conjunction with a hydrophobic membrane, the useful life of that membrane is enhanced by since the flow of fluid to the membrane is blocked. The venting capability of a hydrophobic membrane will typically diminish as the membrane is wetted.

The respective dimensions of the valve housing and the float are such that the float rises readily when the chamber of the housing is filled with a certain amount of fluid. The float is raised to an upper position whereby its upper seal engages the air outlet seat to close or shut off the fluid communications path between the chamber of the housing and the atmosphere. At that time, the lower seal of the float is moved sufficiently far away from the fluid outlet seat so that the fluid inside the housing would flow unhindered out of the fluid outlet. This continues so long as there is a sufficient amount of fluid in the chamber of the housing to keep the float afloat to thereby keep open the fluid path between the chamber of the housing and the fluid outlet, while at the same time closing off the gas outlet.

If gas such as air gets inside the housing, given that gas is lighter than fluid, the gas would form as gas bubbles and float to the top of the fluid. When a sufficient amount or volume of gas is collected in chamber of the housing, the amount of fluid in the chamber is reduced to the point where fluid could no longer buoyantly support the float. As a result, the float falls or moves to a lower position whereby its lower seal engages the fluid outlet seat to thereby shut off the flow of fluid to the patient. At the same time, the gas outlet is opened to vent the gas collected in the chamber of the housing to the atmosphere. So long as the amount of gas or air in the housing is such that the upper seal of the float is disengaged from the seat of the gas outlet, the gas within the housing is vented to the atmosphere. When the gas in the chamber of the housing is reduced to a given amount due to the inflow into the chamber of additional fluid, the float would again rise and its lower seal disengages from the fluid outlet to allow fluid to be output to the patient. When enough fluid flows into the housing without introduction of gas or air therewith, the float is moved to its upper position so that its upper seal shuts off the gas vent to prevent reverse air inflow of air from the atmosphere into the chamber of the housing.

The operation of the gas vent valve assembly of the instant invention is therefore independent of whether there is any power being supplied to the fluid warmer, i.e., whether the fluid warmer is turned on. Rather, the operation of the instant inventive gas vent valve assembly is dependent on the relationship between the volume or amount of gas/air and the volume or amount of fluid in the housing vis-a-vis the density of the float and its buoyancy relative to the fluid inside the chamber of the housing, the viscosity of the fluid, and the positioning of the float relative to the housing in response to the amount of fluid in the chamber of the housing. The performance or operation of the float is also dependent on orientation, i.e. the gas vent valve assembly being attached to the system in a vertical orientation.

The instant invention is therefore an apparatus for preventing gas from being input to a patient who is being infused with an infusate. The apparatus comprises a housing having an inlet to enable the infusate to flow into the housing, a gas outlet to vent gas from the housing and a fluid outlet to output the infusate to the patient. The apparatus further includes an actuator movable inside the housing, the actuator having an upper end and a lower end, an upper seal means being provided at the upper end to seal the gas outlet and a lower seal means at the lower end to seal the gas outlet. The housing of the apparatus has a longitudinal space that enables the actuator to at least move between an upper position whereby the upper seal means seals the gas outlet and the fluid outlet is opened, and a lower position whereby the lower seal means seals the fluid outlet and the gas output is opened. The actuator is moved to the lower position to seal the fluid outlet with the lower seal means and to open the gas outlet to vent the gas inside the housing when a predetermined volume of gas gets inside the housing.

The present invention also is directed to a fluid warmer having a heater, at least one reservoir containing an infusate to be infused to the patient, a fluid communications path for conveying the infusate to the heater for warming with the warmed infusate being output to a gas elimination device to ensure that gas in the warmed infusate is removed. The gas elimination device comprises: a housing having an inlet to enable the infusate to flow into the housing, a gas outlet to vent gas from the housing and a fluid outlet to output the infusate to the patient; and an actuator movable inside the housing that has an upper end and a lower end, the upper end of the actuator having an upper seal for sealing the gas outlet, the lower end of the actuator having a lower seal for sealing the fluid outlet. The actuator is movable between an upper position wherein the upper seal seals the gas outlet and the fluid outlet is opened, and a lower position wherein the lower seal seals the fluid outlet and the gas outlet is opened. And when the gas inside the housing increases to a predetermined volume, the actuator is moved to the lower position to seal the fluid outlet and to open the gas outlet to vent the gas inside the housing out to the atmosphere.

The present invention further is related to a disposable set of fluid transfer tubes that includes a first tubing connectable to at least one infusate reservoir for receiving an infusate, a heat transfer portion of the tubing for transferring heat to the infusate flowing through the tubing, and an output portion for outputting the infusate. The disposable set further comprises: a housing having an inlet connected to the output portion of the tubing to receive the infusate, the housing having a gas outlet to vent gas from the housing and a fluid outlet to output the infusate to the patient; an actuator movable inside the housing having an upper end and a lower end, the upper end having an upper seal for sealing the gas outlet, the lower end having a lower seal for sealing the fluid outlet; wherein the actuator is movable between an upper position wherein the upper seal seals the gas outlet and the fluid outlet is opened and a lower position wherein the lower seal seals the fluid outlet and the gas outlet is opened; and wherein when there is a predetermined volume of gas inside the housing, the actuator is moved to the lower position to seal the fluid outlet and to open the gas outlet to vent the gas inside the housing out of the housing.

The actuator described above may be in the form of a float.

BRIEF DESCRIPTION OF THE FIGURES

The present invention will become apparent and the invention itself will be best understood with reference to the following description of the present invention taken in conjunction with the accompanying drawings, wherein:

FIG. 3 is an air detector which when used with the present invention provides an additional safety feature for preventing gas or air in the infusate from being administered into the patient;

FIG. 5 is a cross-sectional view showing the gas vent valve assembly of the instant invention; and FIG. 6a and FIG. 6b are respective illustrations showing the gas vent valve assembly of the instant invention closing the fluid outlet to prevent fluid flow to the patient and opening the fluid outlet to allow fluid to be infused to the patient.

DETAILED DESCRIPTION OF THE INVENTION

Figure 1:
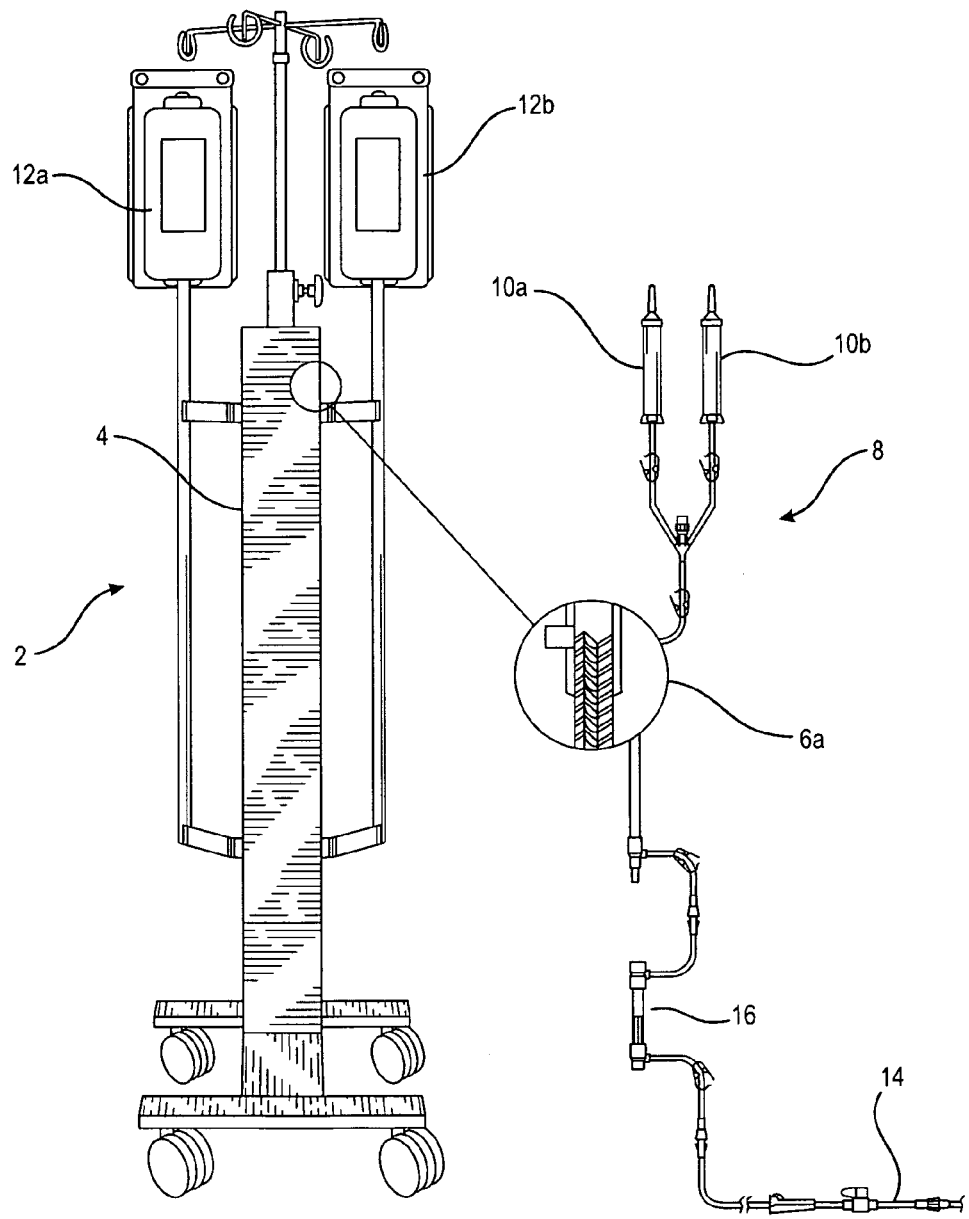
FIG. 1 is a prior art illustration of a fluid warmer and a conventional disposable unit.

With reference to FIG. 1, a prior art fluid warmer, such as for example the System 1025 manufactured by the assignee of the instant application, is shown. The fluid warmer is designated 2 and includes a central portion 4 that has a heater therein for fluidly heating a heat exchanger 6, a portion of which is shown in the exploded view 6a. The heat exchanger 6 is a part of a fluid transfer disposable set 8, for example an intravenous (IV) tube set, that includes bag spikes 10a and 10b that are used to connect to storage bags 12a and 12b, respectively. The storage bags 12a and 12b may be referred to as fluid reservoirs that store cellular or physiological fluids such as for example blood, saline and other well known fluids for infusion into a patient. As the fluid from the fluid reservoir flows through heat exchanger 6, it is heated. This heated fluid is introduced or administered to a patient as an infusate, by means of a tube 14 that has a conventional luer end for connection to a cannula inserted into the patient. A filter 16 is provided in the disposable set to filter out particulates that may be contained in the infusate. The predecessor of the fluid warmer and the disposable set as shown in FIG. 1 are discussed in U.S. Pat. No. 4,759,749, assigned to the assignee of the instant invention. The disclosure of the '749 patent is incorporated herein. The heat exchanger shown in FIG. 1, as well as its operation, are described in U.S. Pat. Nos. 4,878,537, 5,063,994 and 5,097,898, all assigned to the assignee of the instant invention. The respective disclosures of the '537, '994 and '898 patents are incorporated by reference to this application.

Figure 2:
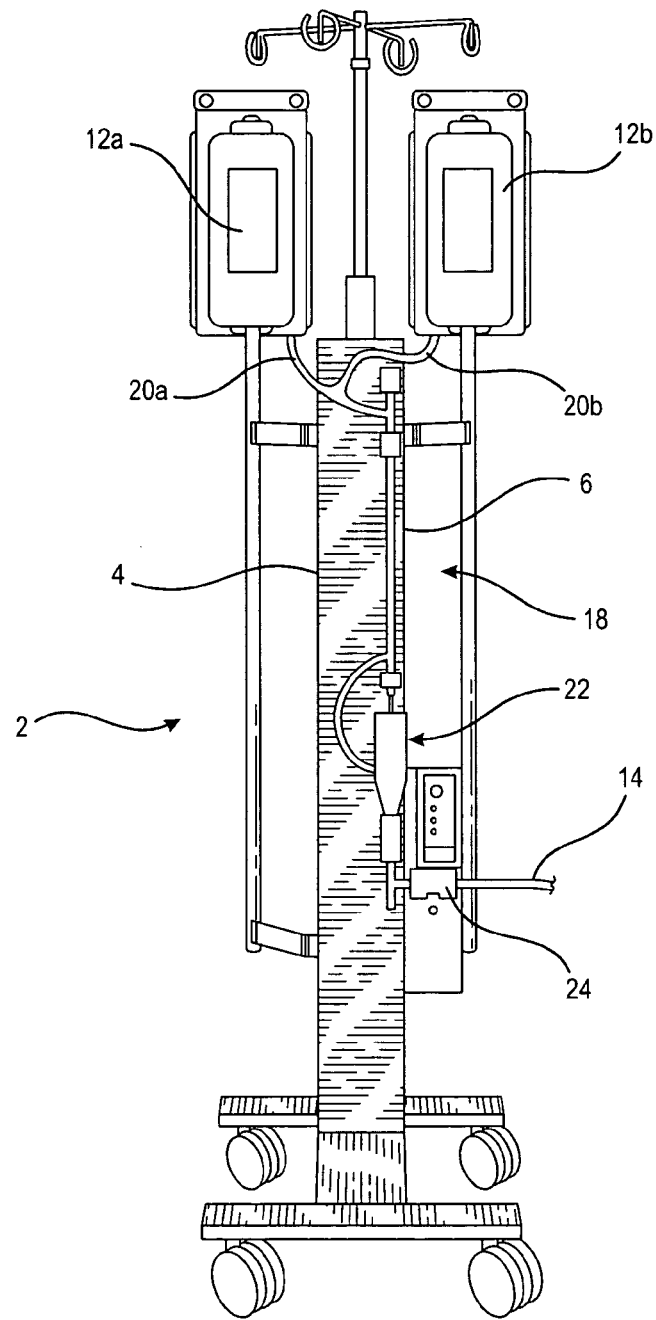
FIG. 2 is an illustration of the present invention gas vent valve assembly integrated to a disposable fluid transfer set of the instant invention assembled to a fluid warmer.

A fluid warmer similar to that shown in FIG. 1 is illustrated in FIG. 2. Elements that are the same as the elements shown in FIG. 1 are labeled the same. For the FIG. 2 fluid warmer, however, there is shown assembled thereto the disposable set of the instant invention, designated 18, which has likewise spikes 20a and 20b for effecting respective fluid communications paths with fluid bags or reservoirs 12a and 12b. There is likewise a heat exchanger 6 mounted to fluid warmer and by which heated water flows for warming the infusate flowing through the heat exchanger.

Although prior art fluid warmers of the assignee have been described herein for the instant invention, it should be appreciated that the gas valve assembly of the instant invention may also be used for other warmers such as for example a fast flow fluid warmer.

For the inventive disposable fluid transfer set 18, a gas vent valve assembly of the instant invention, designated 22, is added thereto for receiving the heated fluid or infusate from heat exchanger 6. The gas vent valve assembly eliminates gas such as air that may somehow have been introduced into the tubing or fluid flow and must be eliminated, as such gas pockets if injected into a patient as an air emboli may cause harm and even death to the patient. The output from the gas vent valve assembly is connected to an air detector 24 which provides a redundant check for the presence of air in the infusate. The outlet is in the form of tubing 14, which, as mentioned previously, is connected to a cannula inserted to the patient so that the fluid may be infused into the patient.

FIG. 3 is an illustration of the air detector that my be used for detecting any potential air emboli present in the fluid to be infused to the patient. The chamber whereby air emboli may be detected is designated 26. For the instant invention, chamber 26 receives the fluid via tubing 28 from the outlet of the gas vent valve assembly of the instant invention.

Figure 4A:
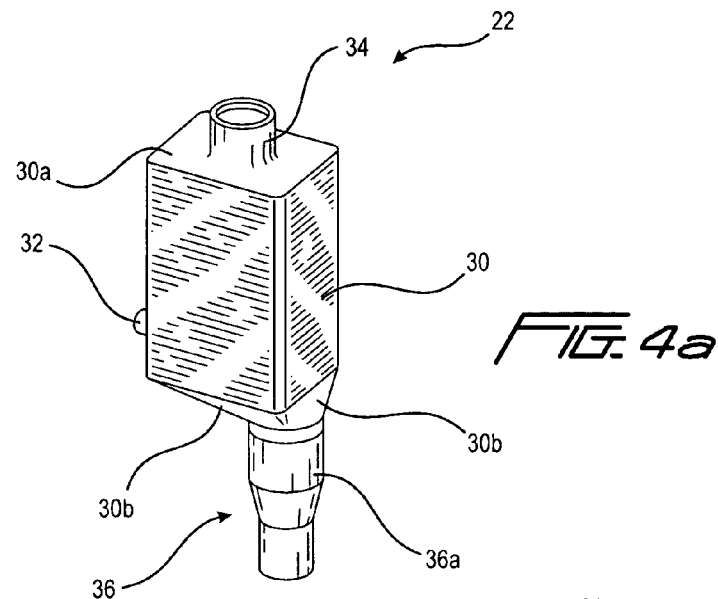
FIG. 4a is an assembled isometric view of the gas vent valve assembly of the instant invention.
Figure 4B:
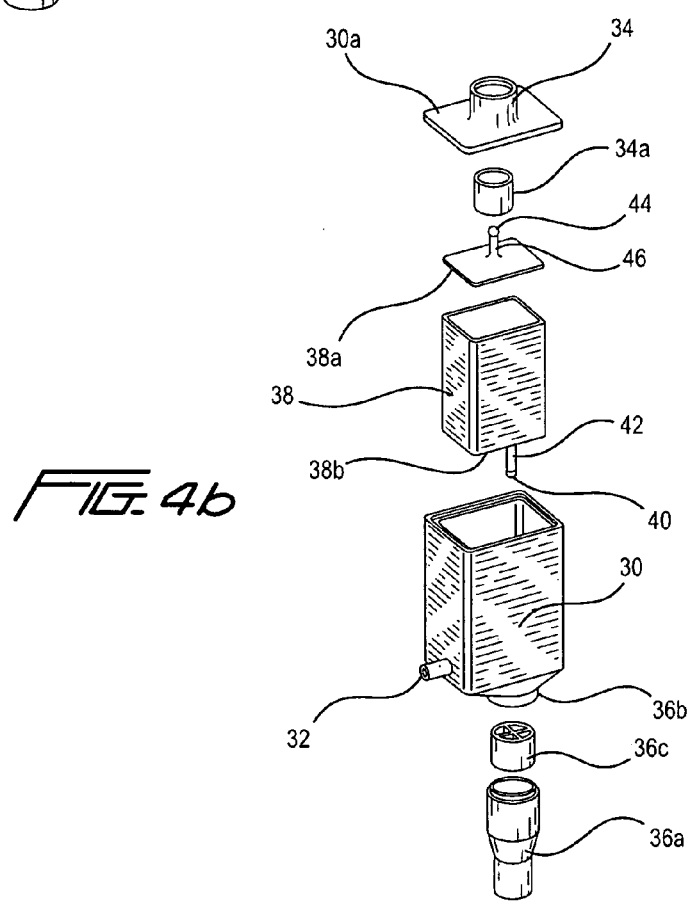
FIG. 4b is an exploded view of the various components that make up the gas vent valve assembly of the instant invention.

With reference to FIGS. 4a and 4b, the gas vent valve assembly 22 of the instant invention is shown to have a valve body or housing 30 that, for the embodiment, is an elongated chamber having substantially rectangular sides but a square top and bottom that is funnel shaped. The top or top surface is designated 30a while the downward slanted bottom surface is designated 30b. There is a fluid inlet 32, located at the lower portion of body 30, that allows the heated infusate to flow into the housing 30. There is at top 30a an air or gas outlet 34 that allows air or gas to output from housing 30 to the atmosphere. As best shown in FIG. 4b, the gas outlet 34, along with its outlet neck that is integrally formed as a one-piece with the top 30a, includes a gas outlet or upper seat 34a that fits within gas outlet 34. Gas outlet seat 34a forms a guide and provides the seat to which a sealing member sits for closing or sealing the opening of gas outlet 34.

There is moreover a fluid outlet 36 extending from the funnel shaped lower portion of the housing 30. Fluid outlet 36 allows the infusate in the chamber of housing 30 to be output to the patient. As best shown in FIG. 4b, the fluid outlet 36 comprises a spout 36a that is connected to a lower neck 36b that extends from the bottom funnel portion of housing 30. As best shown in FIG. 5, with the lower portion of housing 30 being funneled shaped, per designation 30b, the fluid stored in the chamber of the housing is funneled directly into sprout output 36a. The fluid outlet 36 includes a lower seat 36c fitted within a neck 36b and the spout output 36a. Fluid outlet 36 is closed or sealed by corresponding lower sealing member.

As best shown in FIG. 4b, an actuator in the form of a float 38 is movably positioned within the chamber or interior cavity of body 30. Float 38 is of a dimension that enables it to be readily movable within the chamber of housing 30. For the embodiment shown in FIGS. 4a and 4b, float 38 has an elongated body that has rectangular sides along its longitudinal axis and a square top 38a and bottom 38b. A shaft 42 extends from the bottom 38b of float 38. To the distal end of shaft 42 there is attached a seal mechanism that may be in the shape of a ball or a sphere 40, or any other appropriate shape that allows it to sealingly engage lower seat 36c of fluid outlet 36. There is extending from the top 38a of float 38 an upper shaft 46 to which an upper seal mechanism is attached to its distal end. The seal mechanism at the upper shaft 46 may also be in the shape of a ball or a sphere 44, or any other shape that allows it to sealingly engage upper seat 34a of gas outlet 34. Although shown to be removed from float 38 in FIG. 4b, in practice top 38a, as well as bottom 38b, each are welded to and therefore form an integral part of float 38, so that float 38 is completely sealed with an internal cavity and a density that allows it to rise inside the chamber of housing 30 when the level of fluid in the chamber is raised to a given level.

It should be appreciated that the respective cross sections of the housing 30 and float 38 may be configured differently from those shown in FIGS. 4a and 4b. For example, the cross sections of the housing and the float may well be square, rectangular, circular, D-shaped or any other shape so long as those shapes conform to the space available on the surface or portion of the equipment to which the housing is to be attached. The thing to note is the aspect ratio (largest width dimension compared to the height) of the float is important in that it is needed for the proper tracking of the float.

With reference to FIG. 5, a fully assembled gas vent valve assembly of the instant invention is shown. As illustrated, the actuator float 38 is located within housing 30, and is dimensioned such that it is movable longitudinally within the chamber of housing 30. The upper shaft 46 is shown to be extending substantially along the longitudinal axis of the float 38 while the lower shaft 42 is offset from the longitudinal axis of housing 30 so that it is aligned along the longitudinal axis of the fluid outlet 36. Thus, when moving to its upper position, the upper sealing sphere 44 of float 38 is movably guided by the gas vent guide 34a; and when moving to its lower position, the lower sealing sphere 40 of float 30 is movably guided by the fluid outlet guide 36c. When float 30 is moved fully to its upper position, its upper seal sphere 44, guided within guide 34a, would fully sit on or sealingly engage the upper seat 34c to block the opening of seat 34c to thereby close or shut gas vent outlet 34 to prevent any reverse inflow of air from the atmosphere into the housing. At that time or sometime prior to that depending on the dimensions of the float and its upper and lower shafts relative to the dimension of the chamber of housing 30, the fluid outlet is opened. Similarly, when float 30 is moved to its lower position, the lower seal sphere 40 is guided by lower guide 36c to sealingly engage lower seat 36d to block the opening of lower seat 36d to thereby close or shut fluid outlet 36. The gas vent guide 34a and fluid outlet guide 36c may be circular components or sleeves, having a minimum of three features, which act as guides to track the upper shaft 46 and the lower shaft 42 respectively. In cross-section, the gas vent guide and fluid outlet guide may resemble wagon wheels, and the guide features may resemble the spokes.

For the instant invention gas vent valve assembly, the input of fluid into housing 30 via fluid inlet 32 is shown by the directional arrow designated 47, the gas or air output from gas vent outlet 34 is shown by the directional arrow 48, and the fluid output from fluid output 36 is shown by the directional arrow designated 50.

The operation of the gas vent valve assembly is based on the buoyancy of the float relative to the fluid inside the chamber of housing 30, and the relationship between the volume of air and the amount of fluid in the chamber of the housing 30. This is illustrated in FIGS. 6a and 6b.

As shown in FIG. 6a, the fluid or infusate flows into the chamber of housing 30 via the fluid inlet 32, as indicated by directional arrow 47. For the FIG. 6a illustration, the amount of fluid or infusate input to the chamber of housing 30 is indicated by outline 52, while the volume of gas or air in the chamber of housing 30 is designated by outline 54. As gas/air is lighter than the fluid, the air rises to the upper portion of the chamber of housing 30. Given the relationship between the volume of air and the amount of infusate in the chamber of housing 30, due to both the density of actuator float 38 and its relationship to the amount of fluid and air in the chamber of housing 30, there is not enough buoyancy provided by fluid 52 to raise up float 38 from its lower position. As a result, the lower seal 40 attached to float 38 remains seated on the outlet seat 36d of fluid outlet 36. The fluid outlet 36 therefore remains shut off and infusate is prevented from being output from the inventive gas vent valve assembly and administered to the patient. At that time, due to the respective configurations of the actuator float 38 and its upper and lower shafts and attached seal mechanisms, the upper seal sphere 44 is positioned away from seat 34c of gas outlet 34. As a consequence, the gas or air inside housing 30, as indicated by outline 54, is vented to the atmosphere per directional arrow 48 as fluid flows into the chamber of housing 30.

As additional infusate is input via fluid inlet 32 into the chamber of housing 30, given that fluid is heavier than air or gas, gas/air bubbles would percolate up from the fluid into the upper portion of the chamber of housing 30, as gas/air is vented via gas outlet 34 to the atmosphere via the open gas outlet 34. With a given amount of fluid within housing 30, per shown by the fluid outline 52 in FIG. 6b, the relationship between the volume of gas and the amount of fluid, and the buoyancy of the actuator float 38 relative to the fluid, cause the actuator float 38 to rise. This is shown in FIG. 6b where the amount of fluid shown by outline 52 is greater than the volume of air shown by outline 54. In this instance, float 38 rises to move the lower seal 40 away from seat 36b of fluid outlet 36, thereby opening the fluid outlet 36 to enable the infusate in the chamber of housing 30 to output from fluid outlet 36, per directional arrow 50. At that time, as float 38 has risen to a predetermined level so that only a small volume of air remains in the chamber, upper seal 44 sealingly engages upper seat 34c of gas outlet 34, thereby closing the gas outlet to prevent any reverse inflow of air from the atmosphere into the housing. The respective dimensions of housing 30 and float 38, as well as the buoyancy of the float relative to the fluid, may be designed such that substantially all the air in the chamber is flushed out of the chamber to the atmosphere before gas vent 34 is shut off.

For the FIG. 6 embodiment of the instant invention, so long as the relative amount of fluid to air within housing 30 is such that it does not cause float 38 to move downwards to its lower position, gas outlet 34 would remain closed. But as soon as the amount of air reaches a volume that causes float 38 to move downwards to a distance that disengages upper seal 44 from upper seat 34c, the gas vent 34 would open to once again vent the air inside the chamber of housing 30 to atmosphere. And when the amount of air inside the chamber of housing 30 gets to a certain volume, for example as per shown in FIG. 6a, the fluid outlet 36 is closed so as to prevent any fluid or gas from being output from the fluid outlet 36 and possibly injected into the patient.

In another feature of the gas vent valve assembly of the instant invention, the upper seal 44 for gas vent 34 may be removed. Instead, a hydrophobic membrane is mounted over the opening of the gas vent. This feature is feasible in those situations where it is determined that the relative dimensions of the housing 30 and float 38 are such that it is highly unlikely that the small amount of air remaining at the top portion of the chamber of housing 30 would make its way down to the fluid outlet 36 and be output therefrom. For this feature, a one way valve may be added to the gas vent 34 to prevent back flow of air from the atmosphere into the chamber of housing 30.

As noted with respect to FIG. 3, an air detector further down on the fluid communications path provides a redundant check on whether there is any air emboli in the infusate. If there is, the warmer system shuts down.

For the gas vent valve assembly of the instant invention, insofar as its operation is based on the positioning of the float 38 that is dependent on the relationship of the respective amounts of gas and fluid inside the chamber of housing 30, it operates automatically and without any need for external power. Accordingly, the operation of the gas vent valve assembly of the present invention is transparent to the user, is immune from any power outage to the fluid warmer, and will continue to operate even when there is a loss of power to the fluid warmer.

The invention claimed is:

1. Apparatus for preventing gas from being input to a patient being infused with an infusate comprising: a housing having an inlet located at a lower portion of said housing to enable the infusate to flow into said housing from a side of said housing, a gas outlet at a top of said housing to vent gas from said housing and a fluid outlet at a bottom of said housing where the infusate is funneled to output the infusate to the patient; an actuator movable inside said housing, said actuator having an upper end and a lower end; said upper end having an upper seal means thereon for sealing said gas outlet, said lower end having a lower seal means for sealing said fluid outlet; said housing having a longitudinal chamber to accept said actuator, said actuator and said housing having similar respective cross sectional configurations with the cross section of said actuator being smaller than the cross section of said housing to enable said actuator to readily fit into and move freely within and longitudinally along the chamber of said housing between an upper position when the volume of the infusate in said housing has risen to a predetermined level in the upper portion of said housing and substantially above said inlet whereby said upper seal means seals said gas outlet and said fluid outlet is opened and a lower position when the volume of the infusate in said housing has lowered to a certain volume in the lower portion of said housing substantially adjacent to said inlet whereby said lower seal means seals said fluid outlet and said gas outlet is opened, wherein said upper seal means is movably guided by said gas outlet when said actuator is moved to said upper position and wherein said lower seal means is movably guided by said fluid outlet when said actuator is moved to said lower position; and wherein when the gas reaches a predetermined volume inside said housing, said actuator is moved to said lower position to seal said fluid outlet with said lower seal means and to open said gas outlet to vent the gas in said chamber out of said housing.

2. Apparatus of claim 1, wherein said actuator comprises a float having a top and a bottom, said upper seal means extending from the top of said float and said lower seal means extending from the bottom of said float, said upper seal means extending substantially along a longitudinal axis and said lower seal means being offset from the longitudinal axis.

3. Apparatus of claim 2, wherein said float is of a given density such that the movement of said float is dependent on a relationship between the amount of gas and fluid in said housing.

4. Apparatus of claim 1, wherein said housing comprises a bottom funnel portion that extends to said fluid outlet, and wherein said fluid outlet comprises a seat and wherein said lower seal means comprises a lower sphere attached to a shaft that extends from a lower surface of said actuator, said lower sphere filling the seat of said fluid outlet when said actuator is at said lower position.

5. Apparatus of claim 1, wherein said gas outlet comprises a seat and wherein said upper seal means comprises an upper sphere attached to an upper surface of said actuator, said upper sphere filling the seat of said gas outlet when the amount of gas inside said housing is less than the predetermined volume, said actuator being at said upper position.

6. Apparatus of claim 1, wherein said actuator comprises a body freely movable within said housing having an upper shaft extending from its upper end and a lower shaft extending from its lower end, wherein said upper seal means comprises a first spherical seal at the end of said upper shaft away from said actuator and wherein said lower seal means comprises a second spherical seal at the end of said lower shaft away from said actuator.

7. Apparatus of claim 1, wherein said gas comprises air.

8. Apparatus of claim 1, wherein said fluid comprises blood or blood products.

9. Apparatus of claim 1, wherein said fluid comprises an intravenous (IV) fluid.

10. Apparatus of claim 1, further comprising an air detector for receiving the infusate from said fluid outlet to provide a redundant check on whether there is any air emboli present in the infusate.

11. A fluid warmer having at least one reservoir containing an infusate to be infused to a patient, a fluid communications path for conveying the infusate to a heat exchanger for warming, the warmed infusate being output to a gas elimination device to ensure that gas in the warmed infusate is removed, said gas elimination device comprising: a housing having an inlet located at a lower portion of said housing to enable the infusate to flow into said housing from a side of said housing, a gas outlet located at a top of said housing to vent gas from said housing and a fluid outlet located at a bottom of the housing to output the infusate to the patient; an actuator movable inside said housing, said actuator having an upper end and a lower end, said upper end having an upper seal for sealing said gas outlet, said lower end having a lower seal for sealing said fluid outlet, said actuator and said housing having similar cross sectional configurations with the cross section of said actuator being smaller than the cross section of said housing so that said actuator is readily fit into said housing and freely movable between an upper position within said housing when the volume of the infusate in said housing has risen to a predetermined level in the upper portion of said housing and substantially above said inlet wherein said upper seal seals said gas outlet and said fluid outlet is opened and a lower position when the volume of the infusate in said housing has lowered to a certain volume in the lower portion of said housing substantially adjacent to said inlet wherein said lower seal seals said fluid outlet and said gas outlet is opened, wherein said upper seal is movably guided by said gas outlet when said actuator is moved to said upper position and wherein said lower seal is movably guided by said fluid outlet when said actuator is moved to said lower position; and wherein when the gas inside said housing reaches a predetermined volume, said actuator is moved to said lower position to seal said fluid outlet and to open said gas outlet to vent the gas inside said housing out of said housing.

12. Fluid warmer of claim 11, wherein said actuator comprises a float having a top and a bottom, said upper seal extending from the top of said float and said lower seal extending from the bottom of said float, said upper seal extending substantially along a longitudinal axis and said lower seal being offset from the longitudinal axis.

13. Fluid warmer of claim 11, wherein said housing comprises a bottom funnel portion that extends to said fluid outlet so that the bottom of said housing where said fluid outlet is located has a smaller dimension than the rest of said housing, and wherein said fluid outlet comprises a seat and wherein said lower seal comprises a lower sphere attached to a shaft that extends from a lower surface of said actuator, said lower sphere filling the seat of said fluid outlet when said actuator is at said lower position.

14. Fluid warmer of claim 11, wherein said gas outlet comprises a seat and wherein said upper seal comprises an upper sphere attached to an upper surface of said actuator, said upper sphere filling the seat of said gas outlet when the amount of gas inside said housing is less than the predetermined volume, said actuator being at said upper position.

15. Apparatus of claim 11, further comprising an air detector for receiving the infusate from said fluid outlet to provide a redundant check on whether there is any air emboli present in the infusate.

* * * * *